United States Patent [19]
Ciric

[11] 3,950,496
[45] Apr. 13, 1976

[54] SYNTHETIC ZEOLITE ZSM-18

[75] Inventor: Julius Ciric, Pitman, N.J.

[73] Assignee: Mobil Oil Corporation, New York, N.Y.

[22] Filed: Mar. 27, 1975

[21] Appl. No.: 562,734

Related U.S. Application Data

[63] Continuation of Ser. No. 365,020, May 29, 1973, abandoned.

[52] U.S. Cl............ 423/328; 260/448 C; 252/455 Z
[51] Int. Cl.² ................................................. C01B 33/28
[58] Field of Search.................... 423/328, 329, 330; 260/448 C; 252/445 Z

[56] References Cited
UNITED STATES PATENTS

| | | | |
|---|---|---|---|
| 2,950,952 | 8/1960 | Breck................................ | 423/328 |
| 3,308,069 | 3/1967 | Wadlinger et al. ............. | 423/328 X |
| 3,578,398 | 5/1971 | Jenkins.............................. | 423/328 |
| 3,699,139 | 10/1972 | Rubin et al. .................... | 260/448 C |
| 3,832,449 | 8/1974 | Rosinski et al. ................... | 423/328 |

OTHER PUBLICATIONS

Aiello et al., "J. Chem. Soc. (A)," 1970, pp. 1470–1475.

*Primary Examiner*—Edward J. Meros
*Attorney, Agent, or Firm*—C. A. Huggett

[57] ABSTRACT

A new crystalline aluminosilicate zeolite is disclosed which has the following formula in terms of mol ratios of oxides on a water-free basis:

$$0.9 \pm 0.3\ M_{2/n}O : Al_2O_3 : z\ SiO_2$$

wherein M is at least one cation having a valence $n$ and $z$ is at least 10. This zeolite is designated ZSM-18.

7 Claims, No Drawings

SYNTHETIC ZEOLITE ZSM-18

CROSS REFERENCE TO RELATED APPLICATION

This application is a continuation of copending application Ser. No. 365,020, filed May 29, 1973, now abandoned.

DESCRIPTION OF THE PREFERRED EMBODIMENT

This invention relates to a new synthetic zeolite and to a method for preparing the same. The invention also is concerned with a catalytic composition comprising said zeolite and with catalytic conversion in the presence thereof.

Crystalline aluminosilicate zeolites structurally consist basically of an open three-dimensional framework of $SiO_4$ and $AlO_4$ tetrahedra. Such tetrahedra are cross-lined by the sharing of oxygen atoms, so that the ratio of oxygen atoms to the total of the aluminum and silicon atoms is equal to two. The negative electrovalence of tetrahedra containing aluminum is balanced by the inclusion within the crystal of cations, such as alkali or alkaline earth metal ions.

Many zeolites possess a crystal structure having channels of molecular dimensions. The interstitial spaces are generally originally occupied by water of hydration. After at least partial dehydration, these zeolites may be utilized as efficient adsorbents whereby adsorbate molecules are retained within the interstitial spaces. The interstitial dimensions of openings in the crystal lattice limit the size and shape of the molecules that can be adsorbed. A separation of a mixture of various molecules, based upon molecular dimensions, wherein certain molecules are adsorbed by the zeolite while others are excluded from admission is therefore possible. It is such characteristic of many crystalline zeolites that has led to their designation as "molecular sieves".

A large number of synthetic crystalline zeolites have previously been prepared and they are described in the technical literature and in patents. They are distinguishable from each other and from naturally occurring zeolites on the basis of composition, crystal structure and adsorption properties. The existence of a number of zeolites having similar but distinguishable properties advantageously permits the selection of a particular member having optimum properties for a particular use.

In accordance with the present invention, there is provided a new zeolite having a new type lattice. This new zeolite, hereinafter referred to as "zeolite ZSM-18", has been found to possess its own unique properties.

X-ray diffraction powder patterns of a number of samples of ZSM-18 were obtained using standard techniques. The radiation was the K-alpha doublet of copper and a Geiger counter spectrometer with a strip chart pen recorder was used. The peak heights, I, and the position as a function of $2\theta$, where $\theta$ is the Bragg angle, were read from the spectrometer chart. From these, the relative intensities, $$100 I/I_o$$

wherein $I_o$ is the intensity of the strongest line or peak and d(A) observed, the interplanar spacing in A, corresponding to the recorded lines were calculated.

A study and analysis of the results obtained revealed that there are certain of said x-ray lines which are always present in ZSM-18 irrespective of silica to alumina ratio, thermal treatment or cation exchange. These lines can be referred to as the most significant lines and are set forth below in Table 1.

TABLE I

Most Significant Lines for ZSM-18

| 2θ | dA | Relative Intensity |
| --- | --- | --- |
| 7.69 | 11.5 ± .26 | VS |
| 9.51 | 9.3 ± .20 | W |
| 11.20 | 7.9 ± .16 | M-S |
| 13.42 | 6.6 ± .14 | M |
| 17.39 | 5.1 ± .11 | M |
| 18.48 | 4.8 ± .10 | W |
| 19.13 | 4.64 ± .10 | W |
| 20.46 | 4.34 ± .09 | M |
| 21.26 | 4.18 ± .09 | VS |
| 22.39 | 3.97 ± .08 | S |
| 22.92 | 3.88 ± .08 | W |
| 23.41 | 3.80 ± .08 | S |
| 26.94 | 3.31 ± .07 | M |
| 27.53 | 3.24 ± .07 | M |
| 28.52 | 3.13 ± .065 | W |
| 29.18 | 3.06 ± .06 | M |
| 31.16 | 2.87 ± .06 | M |
| 35.92 | 2.50 ± .05 | W |

In the above table, the relative intensity was designated as follows:

| 100 $I/I_o$ | Relative Intensity |
| --- | --- |
| 60–100 | VS |
| 40–60 | S |
| 20–40 | M |
| 10–20 | W |
| 0–10 | VW |

In one embodiment, the present invention is directed to a crystalline synthetic material having the composition, in terms of mol ratios of oxides on a water-free basis:

$$0.9 \pm 0.3\ M_{2/n}O : Al_2O_3 : z\ SiO_2$$

wherein M represents at least one cation having a valence $n$ and $z$ is any value greater than 10 and preferably between 10 and 30, said material being further characterized by the ability to sorb cyclohexane and tributylamine.

In another embodiment, the invention provides for a new crystalline synthetic material lattice and having the composition in terms of mole ratios of oxides in its "as synthesized state":

$$0.9 \pm 0.3\ M_{2/n}O : Al_2O_3 : z\ SiO_2$$

wherein M is a mixture of both alkali metal cations, especially sodium, and tris-quaternary ammonium ions.

The tris-quaternary ammonium ions contained in the as synthesized form of ZSM-18 are introduced by actually crystallizing ZSM-18 from a forming solution containing tris-quaternary ammonium ions. This is accomplished by using a tris-quaternary ammonium hydroxide which is prepared by ion exchanging a tris-quaternary ammonium halide.

ZSM-18 can conveniently be prepared by heating in an aqueous solution a mixture of oxides or of materials whose chemical composition can be represented as mixtures of the oxides $Na_2O$, $Al_2O_3$, $SiO_2$, $H_2O$, and T, wherein T represents 1 mole of a tris-quaternary ammonium hydroxide which is preferably 1,3,4,6,7,9-hexahydro-2,2,5,5,5,8,8-hexamethyl-2H-benzo [1,2,-C:-3,4-C':5,6-C''] tripyrolium trihydroxide. The heating can be carried out from 20° to 150°C for a period of time ranging from 2 to 150 days.

The composition of the reaction mixture, expressed in terms of mole ratios of oxides is as follows:

|  | Broad | Preferred |
|---|---|---|
| $SiO_2/Al_2O_3$ | 10–30 | 15–18 |
| $Na_2O/Al_2O_3$ | .2–5 | 1–2 |
| $H_2O/Al_2O_3$ | 200–1500 | 400–700 |
| $T/Al_2O_3$ | 1–10 | 1–3 |

The product which crystallizes from the hot reaction mixture is separated, suitably by centrifuging or filtration, washed with water until the effluent wash water in equilibrium with the zeolite has a pH of from about 9 to 12. The material, so obtained, is thereafter activated by heating in an inert atmosphere at a temperature in the approximate range of 100° to 600°C.

In making zeolite ZSM-18, the usual method comprises reacting, in aqueous media, sodium aluminate or an amorphous sodium aluminosilicate gel with a solution prepared by addition of colloidal silica to a solution of tris-quaternary ammonium hydroxide. The reaction is carried out in a suitable vessel made, for example, of metal or glass and capable of closure to prevent loss of water. The reaction mixture is initially continuously or periodically stirred to insure homogeneity. After this mixing, agitation may be stopped as it is unnecessary to agitate the reaction mass during the formation and crystallization of the zeolite, although mixing during such latter stages has not been found to be detrimental.

The crystallization procedures can be satisfactorily carried out at temperatures within the range from about 35° to about 200°C. The pressure during crystallization is atmospheric or at least that corresponding to the vapor pressure of water in equilibrium with the mixture of reactants, while temperatures as low as about 35°C may be employed, such lower temperatures require a long reaction period. Preferably, a temperature of approximately 60° to 150°C is employed. Heating is continued until the desired crystalline zeolite product is formed. The zeolite crystals are then separated from the mother liquor and washed, preferably with distilled water, until the effluent wash water in equilibrium with the product has a pH of between about 9 and about 12.

In the synthesis of zeolite ZSM-18, it has been found that the composition of the reaction mixture is critical. Specifically, the presence of tris-quaternary ammonium ions in such mixture has been found to be essential for the production of zeolite ZSM-18. In the absence of such ions no zeolite ZSM-18 was obtained. The crystallization temperature and the length of time the crystallization temperature is maintained are important variables in determining the yield of crystalline material. Under some conditions, for example, too low a temperature for too short a time, no crystalline product is realized. Extreme conditions may also result in the formation of materials other than zeolite ZSM-18.

Another important aspect of the forming solutions is the silica to alumina ratio. It has been found that if the silica to alumina ratio in the forming solution is below 10, i.e. 9 (all other factors being equal), that ZSM-18 will be formed but that it will either be obtained in admixture with other zeolites and/or that it will be unstable at elevated temperatures. If the silica to alumina ratio of the forming solution is maintained within the above set out limits, a pure and stable ZSM-18 will be obtained.

Sodium oxide present in the reaction mixture may be derived from sodium aluminate or an amorphous sodium aluminosilicate gel. The latter is characterized by the following composition:

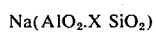

$$Na(AlO_2 \cdot X\ SiO_2)$$

wherein X is a number in the approximate range of 0.5 to 20. This material may be prepared by reaction of methyl orthosilicate and sodium aluminate. Another suitable source of alumina and sodium oxide is a solution of aluminum turnings in sodium hydroxide. Silicate present in the reaction mixture may be derived from a variety of sources, for example, aqueous sodium silicates, silica gel, silica hydrosol, and silicate esters. Thus, silica is desirably introduced into the reaction mixture as a colloidal suspension.

As has previously been stated, ZSM-18 can sorb cyclohexane, thus having a pore size larger than 7A. Zeolite ZSM-18 may be used as an adsorbent in any suitable form. For example, a column of powder crystalline material may afford excellent results as may a pelleted form obtained by pressing into pellets a mixture of the zeolite and a suitable bonding agent, such as clay.

The compositions contemplated herein include not only the sodium form of zeolite ZSM-18 as synthesized above but also crystalline materials obtained from such a zeolite by partial or complete replacement of the original ions with other cations. The original cations can be replaced in accordance with techniques well known in the art, at least in part, by ion exchange with other cations. Preferred replacing cations include metal ions, ammonium ions, hydrogen ions, and mixtures of the same. Particularly preferred cations are those which render the zeolite catalytically active, especially for hydrocarbon conversion. These include hydrogen, rare earth metals, aluminum, metals of Groups II and VIII of the Periodic Table and manganese.

Ion exchange of the zeolite may be accomplished by conventional methods. One continuous method is to pack zeolite ZSM-18 into a series of vertical columns and successively pass through the beds a water solution of the soluble salt of the cation to be introduced into the zeolite; and change the flow from the first bed to the second bed as the zeolite in the first bed becomes ion exchanged to the desired extent. The spatial arrangement of the aluminum, silicon and oxygen atoms which make up the basic crystal lattice of the zeolite remains essentially unchanged by partial or complete substitution of the sodium ion by other cations.

Highly active hydrocarbon conversion catalysts may be obtained by treating the above-described crystalline zeolite ZSM-18 with a fluid medium containing a hydrogen ion or ion capable of conversion to a hydrogen ion in an amount sufficient to impart catalytic properties thereto. The catalysts so obtained possess a wide spectrum in magnitude of catalytic activity; can be used in extremely small concentrations; and permit certain hydrocarbon conversion processes to be carried out under practicable and controllable rates at temperatures much lower than those previously employed. In the catalytic cracking of hydrocarbon oils into hydrocarbon products of lower molecular weight, the reaction rates per unit volume of catalyst that are obtainable by hydrogen treated zeolite ZSM-18 may vary up to several orders of magnitude higher than the rates achieved with siliceous catalysts heretofore proposed. These catalyst furthermore can be used directly as the sole catalytic constituent or as intermediates in the preparation of further modified masses having catalytic properties. Such modified masses may comprise the treated crystalline zeolite per se or a dispersed mixture of the treated aluminosilicates with a predetermined amount of an inert and/or catalytically active material which serves as a binder or matrix for the catalyst constituent. Typical matrices are disclosed in U.S. Pat. Nos. 3,140,249 and 3,140,253. In general, inorganic oxides are preferred.

In order to be used as an absorbent or a catalyst, ZSM-18 should be activated by heating the same at elevated temperatures ranging from about 100°–600°C for a period of time ranging from 1 to 48 hours. The heating or calcining is carried out in an atmosphere such as air, nitrogen, hydrogen, flue gas, etc.

The following examples will illustrate the best mode now contemplated for carrying out this invention.

EXAMPLE 1

Preparation of a Tris-quaternary Ammonium Bromide

The reaction vessel employed was a 3-liter, 4-neck, round bottom flask, equipped with stirrer, reflux condenser, thermometer and gas inlet. Dimethylamine gas is passed through a 5A molecular sieve drying column into a vigorously stirred suspension of 254.4 g hexabromomethylbenzene in 800 ml absolute ethanol which is maintained at 70°C. After several hours of passing dimethylamine, a 1 cc sample is taken into a test tube and water added to it. At some time, the entire suspension becomes water soluble. This point will depend on rate of stirring, gas-bubbling, etc., and can be anywhere between 5–20 hours. After that, stirring and bubbling is continued for another 5 hours. Yield, 200-220 g (theoretical: 216 g of 1,3,4,6,7,9,-hexahydro-2,2,5,5,8,8-hexamethyl-2H-benzo[1,2-C:-3,4-C':5,6-C''] tripyrolium tribromide) which had a purity, by Mohr bromide titration, 70–90%. Without further purification, the material is used to prepare hydroxide via ion-exchange.

EXAMPLE 2

Preparation of tris-quaternary ammonium hydroxide

Into a Dowex-1 resin bed (2.5 inches diameter, 20 inches high) having a capacity of 2.5 gram equivalent weight (gew.), is passed through, 2 gew. of the tribromide, 350 g calculated as 100% pure prepared according to Example 1. About 3 liters of 0.6 – 0.7 N alkaline solution is obtained, 90% of input material recovered. The tris-quaternary ammonium hydroxide has the following formula:

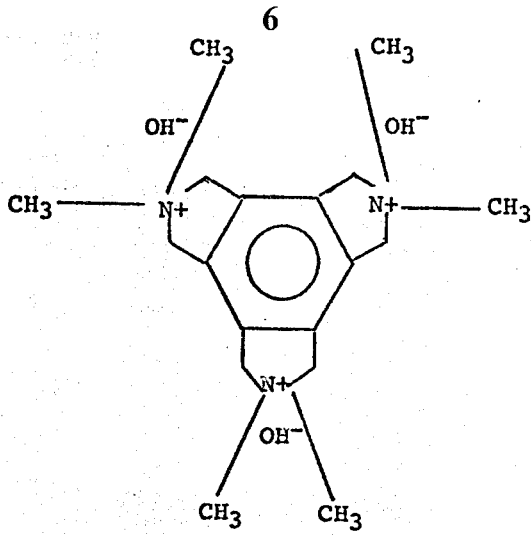

EXAMPLE 3

This example illustrates the preparation of ZSM-18. 7.05 grams of sodium aluminate was dissolved in 277 ml of 0.65N tris-quaternary ammonium hydroxide prepared in accordance with Example 2 and 13.5 ml of water. To the clear aluminate solution was added 68.5 grams of tetramethylorthosilicate and the resulting mixture stirred vigorously until a gel formed.

The gel had the following composition:

$$(2\ T) - 1.14\ Na_2O - Al_2O_3 - 15\ SiO_2 - 500\ H_2O$$

wherein T represents 1 mol of the tris-quaternary ammonium hydroxide.

The above gel was placed in a pressure bomb and heated for 5 days at 125°–130°C. The product was filtered and washed and identified by x-ray analysis as being substantially pure ZSM-18.

The ZSM-18 obtained has the following formula:

$$1.06\ T_{2/3}O:\ 0.09\ Na_2O:\ Al_2O_3:\ 10.6\ SiO_2$$

wherein T represents a tris-quaternary ammonium cation. The zeolite is stable upon heating to 1000°F for 3 hours.

Sorption tests on the above indicated the following results:

| Water | Sorption, Wt. % n-hexane | Cyclohexane |
|---|---|---|
| 21.5 | 14.6 | 14.8 |

EXAMPLE 4

The exact procedure of Example 3 was repeated. Analysis of the product obtained indicated that it had the following formula:

$$1.27\ T_{2/3}:\ 0.07\ Na_2O:\ Al_2O_3:\ 11.5\ SiO_2$$

The above product was identified via x-ray techniques as being essentially pure ZSM-18 and sorption tests indicated the following results:

| Water | Sorption, Wt. % n-hexane | Cyclohexane |
|---|---|---|
| 24.7 | 16.0 | 18.9 |

The ZSM-18 obtained by this technique was stable on being heated for three hours at 1000°F in air.

EXAMPLE 5

The exact procedure of Example 4 was repeated.

Analysis of the product indicated that it had the following formula:

$$1.19\ T_{2/3} : 0.06\ Na_2O : Al_2O_3 : 11.2\ SiO_2$$

The product was identified via x-ray techniques as being pure ZSM-18 and sorption tests had the following results.

| Water | Sorption, Wt. % n-hexane | Cyclohexane |
|---|---|---|
| 23.4 | 15.0 | 14.7 |

This material was also stable upon heating to 1000°F in air for 3 hours.

EXAMPLE 6

This example will illustrate the preparation of ZSM-18 using a forming solution other than that which falls within the range set forth in the specification. The following solutions were prepared:
1. 162 grams of finely divided silica and 3400 ml of tris-quaternary ammonium hydroxide (prepared in accordance with Example 2) 0.8N;
2. 70.5 grams of sodium aluminate and 540 ml of water.

Solution (1) was kept at 50°C for 4 hours to obtain a nearly clear solution and then solution (2) was added. The solutions were mixed together and poured into a 1 gallon autoclave. The starting gel which was obtained had the following composition expressed in mole ratios of oxides.

| | |
|---|---|
| $SiO_2/Al_2O_3$ | 910 |
| $Na_2O/Al_2O_3$ | 1.14 |
| $H_2O/Al_2O_3$ | 670 |
| $T/Al_2O_3$ | 3.0 | wherein T represents 1 mol of tris-quaternary ammonium cation.

The gel was heated in a 1-gallon autoclave and stirred at 135°C for 5 days. The product was filtered, washed and dried at 120°C and then subjected to x-ray analysis.

X-ray analysis of the above material indicated that it had the x-ray diffraction pattern of ZSM-18.

However, upon heating of the above crystalline product to 1000°F in air for 3 hours, the mixture was unstable and substantially reduced to the amorphous state. As can be seen from the ratio of the materials in the forming solution, a silica to alumina ratio of only 9.0 was present, thereby resulting in the formation of an unstable zeolite in this case.

EXAMPLE 7

This example will also illustrate the preparation of a mixture of zeolites which is substantially ZSM-18.

The following solutions were prepared:
1. 27 g Cab-o-sil + 400 ml 0.9 N aqueous tris-quaternary ammonium hydroxide;
2. 11.7 g Na-aluminate + 100 ml 0.9 N aqueous tris-quaternary ammonium hydroxide.

Solution (1) was prepared by adding finely divided silica (commercial brand Cab-o-sil, Cabot Corp.) to 0.9 N aqueous tris-quaternary ammonium hydroxide. The colloidal suspension of silica was allowed to stand at room temperature for 7–10 days until a clear solution was obtained. Solution (2) was then added to solution (1) to obtain a mixture of the following molar composition:

$$3\ T - 1.14\ Na_2O - Al_2O_3 - 9\ SiO_2\ 526\ H_2O$$

(where T equals 1 mol of tris-quaternary ammonium hydroxide). The mixture was held in a bomb at 135°C for 3 weeks. The final product had the following analysis: $0.77\ T_{2/3}O\ 0.25\ Na_2O - Al_2O_3 - 7.9\ SiO_2$.

Upon subjecting the material to x-ray diffraction analysis, it was discovered that a mixture of zeolites was obtained which predominated in ZSM-18 (over 80 wt. %) but contained minor amounts of analcite. It is to be immediately understood, however, that such mixture of zeolites does, indeed, have utility and in order to illustrate the fact, the product obtained from this example was converted to the ammonium form by first exchanging with silver nitrate and then treating the silver form with ammonium thiocyanate. The ammonium form was calcined at 1000°–1100°F for 2 hours to yield a hydrogen form which retained good crystallinity when subjected to x-ray analysis. The sample was found to adsorb 14.5 percent by weight cyclohexane and 20 weight percent water.

The above hydrogen form of the mixture predominating in ZSM-18 was tested for the catalytic cracking of normal hexane by means of an alpha test and found to have an alpha value of 20,173 at 600°F (*Journal of Catalysis*, Vol. IV, No. 4, August, 1965 pages 527–529).

The ZSM-18 zeolites prepared in accordance with Examples 3–7 were subjected to conventional x-ray diffraction analysis in accordance with the techniques previously set forth. It was ascertained that ZSM-18, i.e. may be indexed in the hexagonal crystal system with lattice parameters $a=13.2 + 0.3A$ and $c=15.8 + 0.3A$.

The d spacings obtained from Examples 3–7 are shown below:

TABLE 2

| Example 3 | | Example 4 | | Example 5 | | Example 6 | | Example 7 | |
|---|---|---|---|---|---|---|---|---|---|
| d | $I/I_o$ | d | $I/I_o$ | d | $I/I_o$ | d | $I/I_o$ | d | $I/I_o$ |
| 11.48 | 100 | 11.48 | 100 | 11.56 | 100 | 11.53 | 100 | 11.56 | 96 |
| 9.30 | 15 | 9.29 | 17 | 9.31 | 17 | 9.31 | 11 | 9.31 | 18 |
| 7.94 | 25 | 7.94 | 33 | 7.91 | 26 | 7.96 | 22 | 7.94 | 55 |
| 6.61 | 20 | 6.61 | 24 | 6.61 | 26 | 6.62 | 35 | 6.63 | 29 |
| 6.51 | 38 | 6.51 | 44 | 6.51 | 41 | 6.52 | 22 | 6.53 | 67 |
| 6.10 | 5 | 6.10 | 5 | 6.11 | 5 | 6.13 | 4 | 6.12 | 4 |
| 5.72 | 3 | 5.72 | 2 | 5.74 | 2 | 5.74 | 6 | 5.74 | 5 |
| — | — | — | — | — | — | — | — | 5.61 | 9 |
| 5.37 | 3 | 5.37 | 3 | 5.37 | 1 | 5.41 | 4 | 5.40 | 1 |

TABLE 2-continued

| Example 3 d | $I/I_o$ | Example 4 d | $I/I_o$ | Example 5 d | $I/I_o$ | Example 6 d | $I/I_o$ | Example 7 d | $I/I_o$ |
|---|---|---|---|---|---|---|---|---|---|
| 5.08 | 25 | 5.07 | 24 | 5.08 | 22 | 5.09 | 20 | 5.09 | 29 |
| — | — | — | — | — | — | — | — | 4.90 | 3 |
| 4.79 | 15 | 4.79 | 16 | 4.79 | 14 | 4.81 | 11 | 4.80 | 25 |
| 4.63 | 17 | 4.63 | 19 | 4.64 | 15 | 4.65 | 13 | 4.65 | 20 |
| 4.33 | 25 | 4.32 | 25 | 4.33 | 21 | 4.34 | 24 | 4.34 | 22 |
| 4.17 | 80 | 4.17 | 94 | 4.18 | 73 | 4.19 | 80 | 4.19 | 80 |
| 4.13 | 67 | 4.12 | 60 | 4.12 | 64 | 4.14 | 52 | 4.13 | 100 |
| 3.95 | 38 | 3.95 | 44 | 3.95 | 33 | 3.98 | 35 | 3.97 | 80 |
| 3.88 | 17 | 3.88 | 22 | 3.88 | 17 | 3.90 | 17 | 3.89 | 18 |
| 3.80 | 50 | 3.80 | 59 | 3.80 | 47 | 3.79 | 46 | 3.81 | 49 |
| 3.74 | 5 | 3.73 | 6 | 3.74 | 5 | — | — | 3.75 | 11 |
| — | — | — | — | — | — | — | — | 3.66 | 5 |
| 3.44 | 10 | 3.44 | 8 | 3.44 | 9 | 3.45 | 11 | 3.45 | 18 |
| 3.34 | 15 | 3.34 | 19 | 3.35 | 17 | 3.36 | 14 | 3.36 | 23 |
| 3.31 | 24 | 3.31 | 24 | 3.31 | 21 | 3.31 | 21 | 3.33 | 20 |
| 3.24 | 20 | 3.23 | 20 | 3.24 | 20 | 3.24 | 23 | 3.25 | 21 |
| 3.17 | 2 | 3.18 | 2 | 3.18 | 3 | 3.16 | 4 | 3.19 | 3 |
| 3.12 | 15 | 3.11 | 14 | 3.12 | 14 | 3.12 | 16 | 3.13 | 17 |
| 3.05 | 22 | 3.05 | 26 | 3.05 | 22 | 3.06 | 20 | 3.06 | 38 |
| 2.95 | 3 | 2.95 | 6 | 2.95 | 4 | 2.97 | 5 | 2.97 | 5 |
| 2.92 | 9 | 2.92 | 10 | 2.92 | 8 | 2.94 | 11 | 2.93 | 22 |
| 2.86 | 17 | 2.86 | 20 | 2.86 | 16 | 2.87 | 23 | 2.87 | 25 |
| 2.80 | 5 | 2.80 | 4 | 2.80 | 4 | 2.81 | 4 | 2.81 | 5 |
| 2.77 | 3 | 2.77 | 3 | 2.78 | 3 | 2.78 | 5 | 2.78 | 5 |
| 2.75 | 4 | 2.75 | 5 | 2.75 | 7 | 2.76 | 5 | 2.76 | 9 |
| 2.72 | 3 | 2.72 | 5 | 2.72 | 6 | 2.73 | 6 | 2.73 | 7 |
| 2.69 | 5 | 2.69 | 5 | 2.69 | 6 | 2.70 | 4 | 2.70 | 7 |
| 2.63 | 5 | 2.63 | 6 | 2.63 | 6 | 2.64 | 5 | 2.64 | 7 |
| 2.59 | 2 | 2.60 | 2 | 2.59 | 2 | 2.60 | 4 | 2.60 | 3 |
| 2.56 | 5 | 2.55 | 8 | 2.55 | 6 | 2.57 | 6 | 2.56 | 11 |
| — | — | 2.54 | 2 | 2.53 | 3 | — | — | — | — |
| 2.50 | 9 | 2.50 | 10 | 2.50 | 11 | 2.51 | 10 | 2.51 | 11 |
| 2.47 | 2 | 2.47 | 2 | 2.47 | 3 | 2.48 | 3 | 2.48 | 2 |
| — | — | 2.45 | 2 | 2.44 | 2 | — | — | 2.45 | 2 |
| 2.38 | 3 | 2.38 | 3 | 2.39 | 3 | 2.39 | 3 | 2.39 | 3 |
| 2.35 | 3 | 2.35 | 4 | 2.35 | 3 | 2.36 | 4 | 2.36 | 4 |
| 2.29 | 2 | 2.29 | 2 | 2.29 | 2 | 2.29 | 2 | 2.30 | 2 |
| 2.26 | 4 | 2.25 | 4 | 2.25 | 4 | 2.27 | 4 | 2.26 | 5 |
| 2.20 | 2 | 2.19 | 2 | 2.19 | 2 | 2.20 | 3 | 2.21 | 2 |
| 2.17 | 3 | 2.17 | 2 | 2.16 | 2 | 2.18 | 3 | 2.19 | 2 |
| 2.14 | 5 | 2.14 | 5 | 2.14 | 4 | 2.15 | 5 | 2.17 | 3 |
| 2.12 | 4 | 2.12 | 3 | 2.12 | 4 | 2.13 | 4 | 2.14 | 5 |
| 2.10 | 1 | 2.10 | 2 | 2.09 | 2 | 2.11 | 3 | 2.13 | 3 |
| — | — | 2.08 | 1 | — | — | — | — | 2.11 | 1 |
| 2.06 | 3 | 2.06 | 5 | 2.06 | 4 | 2.06 | 4 | 2.06 | 5 |
| 2.03 | 5 | 2.03 | 5 | 2.03 | 5 | 2.04 | 4 | 2.04 | 5 |
| 2.01 | 3 | 2.00 | 2 | 2.00 | 3 | 2.01 | 3 | 2.01 | 2 |
| 1.96 | 1 | 1.96 | 1 | 1.96 | 1 | 1.97 | 2 | 1.96 | 1 |
| 1.91 | 2 | 1.91 | 2 | 1.92 | 2 | 1.91 | 8 | 1.92 | 3 |
| 1.90 | 7 | 1.90 | 7 | 1.90 | 6 | — | — | 1.90 | 10 |
| 1.87 | 5 | 1.87 | 4 | 1.87 | 5 | 1.87 | 5 | 1.87 | 6 |

From the above data, it can be seen that Example 7 was not pure ZSM-18 and this is indicated by the presence of extra lines at 5.61, 4.90 and 3.66.

The x-ray lines of 3, 4, 5 and 6 are substantially identical even though the ZSM-18 zeolite of Example 6 was unstable at 1000°F.

It is noted that the zeolite produced by Example 6 does, indeed, have utility as an adsorbent as well as a catalyst (upon ion exchange with hydrogen ions or metal ions). This zeolite must be used at temperatures below 900°F and more preferably below 600°F. A typical reaction for which this zeolite is useful is in the conversion of olefins.

The high silica ZSM-18 i.e. Examples 3, 4 and 5 have the same utility, i.e. hydrocarbon conversion catalysts and adsorbents, but can be used at higher temperatures i.e. 1000°F or higher if desired.

As has previously been set forth, low silica ZSM-18 zeolites are produced in the manner set forth in the specification with the exception that the $SiO_2/Al_2O_3$ of the forming solution is at least 5 and less than 10. The ZSM-18 zeolites so obtained have a silica to alumina ratio of from 5 to less than 10.

What is claimed is:

1. A crystalline synthetic aluminosilicate having the composition expressed in terms of mole ratios of oxides $$0.9 \pm 0.3 \, M_{2/n}O : Al_2O_3 : z \, SiO_2$$

wherein M represents at least one cation having a valence $n$ and $z$ is 10–30, said aluminosilicate having the x-ray diffraction lines as shown in Table 1.

2. A thermally treated aluminosilicate as defined in claim 1 wherein said thermal treatment is carried out at about 100°–600°C for at least 1 hour.

3. The composition of claim 1 wherein at least some M is sodium.

4. The composition of claim 1 wherein at least some M is rare earth.

5. The composition of claim 1 wherein at least some M is a hydrogen ion.

6. The composition of claim 1 wherein M is a mixture of hydrogen and metal ions.

7. The composition of claim 1 wherein at least some M is a tris-quaternary ammonium ion derived from 1,3,4,6,7,9-hexahydro-2,2,5,5,5,8,8-hexamethyl-2H-benzo (1,2,-C:-3,4-C' :5,6-C'') tripyrolium trihydroxide.

* * * * *